(12) United States Patent
Hendrick (10) Patent No.: US 10,987,168 B2
(45) Date of Patent: Apr. 27, 2021

(54) SYSTEM AND METHOD FOR COORDINATED LASER DELIVERY AND IMAGING

(71) Applicant: THE SPECTRANETICS CORPORATION, Colorado Springs, CO (US)

(72) Inventor: Brandon Thomas Hendrick, Colorado Springs, CO (US)

(73) Assignee: SPECTRANETICS LLC, Colorado Springs, CO (US)

( * ) Notice: Subject to any disclaimer, the term of this patent is extended or adjusted under 35 U.S.C. 154(b) by 253 days.

(21) Appl. No.: 16/279,384

(22) Filed: Feb. 19, 2019

(65) Prior Publication Data

US 2019/0175274 A1     Jun. 13, 2019

Related U.S. Application Data (63) Continuation of application No. 14/723,956, filed on May 28, 2015, now abandoned.

(Continued)

(51) Int. Cl.
*A61B 18/24*        (2006.01)
*A61B 8/12*         (2006.01)
(Continued)

(52) U.S. Cl.
CPC ........ *A61B 18/245* (2013.01); *A61B 1/00006* (2013.01); *A61B 1/045* (2013.01);
(Continued)

(58) Field of Classification Search
CPC ... A61B 18/245; A61B 1/045; A61B 1/00006; A61B 5/0084; A61B 18/24; A61B 8/12;
(Continued)

(56) References Cited

U.S. PATENT DOCUMENTS 4,053,845 A    10/1977   Gould
4,327,738 A *   5/1982   Green .................... A61B 1/042
                                                           348/65

(Continued)

FOREIGN PATENT DOCUMENTS

EP         0211984 B2    3/1987
EP         2319404 B1    5/2011
(Continued)

OTHER PUBLICATIONS

Mond et al. The Electrode-Tissue Interface: The Revolutionary Role of Steroid Elution; Pace vol. 15, Jan. 1992, pp. 95-107.
(Continued)

*Primary Examiner* — Rene T Towa (57) ABSTRACT

The present disclosure relates to a system and method for coordinated laser delivery and imaging during an interventional procedure. A method may include activating an imaging source to provide a pulsed imaging signal and activating a laser source to provide a pulsed laser signal while the imaging source remains activated. The method may include coordinating the pulsed laser signal and the pulsed imaging signal to output each pulse of the pulsed laser signal and each pulse of the pulsed imaging signal in non-overlapping time windows. A system may include a controller in communication with the laser source and the imaging source for coordinating the output of the laser signal and the imaging signal.

17 Claims, 5 Drawing Sheets

Related U.S. Application Data (60) Provisional application No. 62/004,666, filed on May 29, 2014.

(51) Int. Cl.
| | |
|---|---|
| *A61B 5/00* | (2006.01) |
| *A61B 1/045* | (2006.01) |
| *A61B 1/00* | (2006.01) |
| A61B 18/00 | (2006.01) |
| A61B 1/06 | (2006.01) |
| A61B 8/00 | (2006.01) |
| A61B 34/20 | (2016.01) |

(52) U.S. Cl.
CPC .............. *A61B 5/0084* (2013.01); *A61B 8/12* (2013.01); *A61B 18/24* (2013.01); *A61B 1/06* (2013.01); *A61B 8/445* (2013.01); *A61B 2018/00404* (2013.01); *A61B 2018/00577* (2013.01); *A61B 2018/00702* (2013.01); *A61B 2018/00928* (2013.01); *A61B 2018/00982* (2013.01); *A61B 2034/2065* (2016.02)

(58) Field of Classification Search
CPC ... A61B 1/06; A61B 8/445; A61B 2034/2065; A61B 2018/00577; A61B 2018/00702; A61B 2018/00928; A61B 2018/00982; A61B 2018/00404; A61B 2090/306; A61B 2090/3784; A61B 2017/00176
See application file for complete search history.

(56) References Cited

U.S. PATENT DOCUMENTS

| | | |
|---|---|---|
| 4,641,912 A | 2/1987 | Goldenberg |
| 4,669,465 A | 6/1987 | Moore et al. |
| 4,686,979 A | 8/1987 | Gruen et al. |
| 4,732,448 A | 3/1988 | Goldenberg |
| 4,747,405 A | 5/1988 | Leckrone |
| 4,769,005 A | 9/1988 | Ginsburg et al. |
| 4,784,132 A | 11/1988 | Fox et al. |
| 4,788,975 A | 12/1988 | Shturman et al. |
| 4,799,754 A | 1/1989 | Goldenberg |
| 4,807,620 A | 2/1989 | Strul et al. |
| 4,830,460 A | 5/1989 | Goldenberg |
| 4,844,062 A | 7/1989 | Wells |
| 4,848,336 A | 7/1989 | Fox et al. |
| 4,850,686 A | 7/1989 | Morimoto et al. |
| 4,913,142 A | 4/1990 | Kittrell et al. |
| 4,919,508 A | 4/1990 | Grace et al. |
| 4,924,863 A | 5/1990 | Sterzer |
| 4,925,265 A | 5/1990 | Rink et al. |
| 5,016,964 A | 5/1991 | Donnelly |
| 5,024,234 A | 6/1991 | Leary et al. |
| 5,026,366 A | 6/1991 | Leckrone |
| 5,034,010 A | 7/1991 | Kittrell et al. |
| 5,040,548 A | 8/1991 | Yock |
| 5,041,108 A | 8/1991 | Fox et al. |
| 5,047,952 A | 9/1991 | Kramer et al. |
| 5,109,276 A * | 4/1992 | Nudelman ......... A61B 1/00193 348/47 |
| 5,154,680 A | 10/1992 | Drzewiecki et al. |
| 5,165,897 A | 11/1992 | Johnson |
| 5,176,674 A | 1/1993 | Hofmann |
| 5,188,632 A | 2/1993 | Goldenberg |
| 5,207,672 A | 5/1993 | Roth et al. |
| 5,217,454 A | 6/1993 | Khoury |
| 5,250,045 A | 10/1993 | Bohley |
| 5,263,953 A | 11/1993 | Bagby |
| 5,267,341 A | 11/1993 | Shearin |
| 5,300,085 A | 4/1994 | Yock |
| 5,304,171 A | 4/1994 | Gregory et al. |
| 5,318,032 A | 6/1994 | Lonsbury et al. |
| 5,350,375 A | 9/1994 | Deckelbaum et al. |
| 5,350,377 A | 9/1994 | Winston et al. |
| 5,350,395 A | 9/1994 | Yock |
| 5,352,197 A | 10/1994 | Hammersmark et al. |
| 5,377,683 A | 1/1995 | Barken |
| 5,395,361 A | 3/1995 | Fox et al. |
| 5,400,428 A | 3/1995 | Grace |
| 5,415,653 A | 5/1995 | Wardle et al. |
| 5,423,740 A | 6/1995 | Sullivan et al. |
| 5,425,355 A | 6/1995 | Kulick |
| 5,429,604 A | 7/1995 | Hammersmark et al. |
| 5,429,617 A | 7/1995 | Hammersmark et al. |
| 5,440,664 A | 8/1995 | Harrington et al. |
| 5,451,233 A | 9/1995 | Yock |
| 5,456,680 A | 10/1995 | Taylor et al. |
| 5,464,395 A | 11/1995 | Faxon et al. |
| 5,470,330 A | 11/1995 | Goldenberg et al. |
| 5,484,433 A | 1/1996 | Taylor et al. |
| 5,492,131 A | 2/1996 | Galel |
| 5,514,128 A | 5/1996 | Hillsman et al. |
| 5,536,242 A | 7/1996 | Willard et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,657,760 A | 8/1997 | Ying et al. |
| 5,722,972 A | 3/1998 | Power et al. |
| 5,755,714 A | 5/1998 | Murphy-Chutorian |
| 5,792,118 A | 8/1998 | Kurth et al. |
| 5,800,350 A | 9/1998 | Coppleson et al. |
| 5,803,083 A | 9/1998 | Buck et al. |
| 5,807,377 A | 9/1998 | Madhani et al. |
| 5,817,144 A | 10/1998 | Gregory |
| 5,824,026 A | 10/1998 | Diaz |
| 5,830,209 A | 11/1998 | Savage et al. |
| 5,836,946 A | 11/1998 | Diaz et al. |
| RE36,104 E | 2/1999 | Solar |
| 5,891,133 A | 4/1999 | Murphy-Chutorian |
| 5,938,609 A | 8/1999 | Pomeranz |
| 5,976,124 A | 11/1999 | Reiser |
| 5,986,643 A | 11/1999 | Harvill et al. |
| 5,989,243 A | 11/1999 | Goldenberg |
| 6,022,342 A | 2/2000 | Mukherjee |
| 6,033,402 A | 3/2000 | Tu et al. |
| 6,036,715 A | 3/2000 | Yock |
| 6,056,743 A | 5/2000 | Ellis et al. |
| 6,066,130 A | 5/2000 | Gregory et al. |
| 6,117,128 A | 9/2000 | Gregory |
| 6,231,563 B1 | 5/2001 | White et al. |
| 6,287,297 B1 | 9/2001 | Woodruff et al. |
| 6,290,668 B1 | 9/2001 | Gregory et al. |
| 6,302,875 B1 | 10/2001 | Makower et al. |
| 6,334,846 B1 * | 1/2002 | Ishibashi ................ A61B 5/055 600/439 |
| 6,370,411 B1 | 4/2002 | Osadchy et al. |
| 6,419,684 B1 | 7/2002 | Heisler et al. |
| 6,432,115 B1 | 8/2002 | Mollenauer et al. |
| 6,447,504 B1 | 9/2002 | Ben-Haim et al. |
| 6,447,525 B2 | 9/2002 | Follmer et al. |
| 6,458,098 B1 | 10/2002 | Kanesaka |
| 6,539,132 B2 | 3/2003 | Gennadii Ivtsenkov et al. |
| 6,575,993 B1 | 6/2003 | Yock |
| 6,597,829 B2 | 7/2003 | Cormack |
| 6,733,495 B1 | 5/2004 | Bek et al. |
| 6,743,208 B1 | 6/2004 | Coyle |
| 6,792,390 B1 | 9/2004 | Burnside et al. |
| 7,238,178 B2 | 7/2007 | Maschke |
| 7,319,566 B2 | 1/2008 | Prince et al. |
| 7,568,619 B2 | 8/2009 | Todd et al. |
| 7,572,254 B2 | 8/2009 | Hebert et al. |
| 7,846,153 B2 | 12/2010 | Hebert et al. |
| 7,930,065 B2 | 4/2011 | Larkin et al. |
| 7,959,608 B2 | 6/2011 | Nash et al. |
| 7,988,633 B2 | 8/2011 | Hossack et al. |
| 8,016,745 B2 | 9/2011 | Hassler et al. |
| 8,016,748 B2 | 9/2011 | Mourlas et al. |
| 8,050,739 B2 | 11/2011 | Eck et al. |
| 8,100,893 B2 | 1/2012 | Dadisman |
| 8,361,097 B2 | 1/2013 | Patel et al. |

(56) References Cited

U.S. PATENT DOCUMENTS

| | | |
|---|---|---|
| 8,545,488 B2 | 10/2013 | Taylor et al. |
| 8,628,519 B2 | 1/2014 | Taylor et al. |
| 2001/0014805 A1 | 8/2001 | Burbank et al. |
| 2002/0013572 A1 | 1/2002 | Berlin |
| 2002/0026118 A1 | 2/2002 | Govari |
| 2002/0045811 A1 | 4/2002 | Kittrell et al. |
| 2002/0103459 A1 | 8/2002 | Sparks et al. |
| 2002/0107445 A1 | 8/2002 | Govari |
| 2002/0159685 A1 | 10/2002 | Cormack |
| 2003/0032936 A1 | 2/2003 | Lederman |
| 2003/0045798 A1 | 3/2003 | Hular et al. |
| 2003/0078566 A1 | 4/2003 | Elliott et al. |
| 2003/0204185 A1 | 10/2003 | Sherman et al. |
| 2003/0219202 A1 | 11/2003 | Loeb et al. |
| 2004/0010204 A1 | 1/2004 | Weber et al. |
| 2004/0059280 A1 | 3/2004 | Makower et al. |
| 2004/0075919 A1 | 4/2004 | Diaz et al. |
| 2004/0111016 A1 | 6/2004 | Casscells et al. |
| 2004/0127889 A1 | 7/2004 | Zhang et al. |
| 2004/0133154 A1 | 7/2004 | Flaherty et al. |
| 2004/0162548 A1 | 8/2004 | Reiser |
| 2005/0004453 A1 | 1/2005 | Tearney et al. |
| 2005/0149176 A1 | 7/2005 | Heggestuen et al. |
| 2005/0203416 A1 | 9/2005 | Angelsen et al. |
| 2006/0020260 A1 | 1/2006 | Dover et al. |
| 2006/0094930 A1 | 5/2006 | Sparks et al. |
| 2006/0217695 A1 | 9/2006 | DeBenedictis et al. |
| 2007/0060879 A1 | 3/2007 | Weitzner et al. |
| 2007/0106289 A1 | 5/2007 | O'Sullivan |
| 2007/0115152 A1 | 5/2007 | Bjorklund et al. |
| 2008/0019657 A1 | 1/2008 | Maitland et al. |
| 2008/0106388 A1 | 5/2008 | Knight |
| 2008/0108867 A1 | 5/2008 | Zhou |
| 2008/0154296 A1 | 6/2008 | Taylor et al. |
| 2009/0177095 A1 | 7/2009 | Aeby et al. |
| 2009/0203989 A1 | 8/2009 | Burnside et al. |
| 2010/0114081 A1 | 5/2010 | Keeler et al. |
| 2010/0152717 A1 | 6/2010 | Keeler |
| 2010/0200076 A1 | 8/2010 | Hieb et al. |
| 2011/0160681 A1 | 6/2011 | Dacey et al. |
| 2011/0196291 A1 | 8/2011 | Vischer et al. |
| 2011/0224649 A1 | 9/2011 | Duane et al. |
| 2011/0270091 A1 | 11/2011 | Hossack et al. |
| 2012/0181331 A1 | 7/2012 | Beden et al. |
| 2012/0253360 A1 | 10/2012 | White et al. |
| 2012/0302828 A1 | 11/2012 | Toledo-Crow et al. |
| 2013/0131579 A1 | 5/2013 | Mantell et al. |
| 2013/0253490 A1 | 9/2013 | Bitzer et al. |
| 2013/0338500 A1 | 12/2013 | Taylor et al. |
| 2014/0114298 A1 | 4/2014 | Taylor et al. |
| 2014/0275982 A1 | 9/2014 | Hendrick et al. |
| 2014/0276603 A1 | 9/2014 | Magee et al. |
| 2014/0276689 A1 | 9/2014 | Grace |
| 2014/0276690 A1 | 9/2014 | Grace |
| 2016/0183804 A1 | 6/2016 | Kowalewski et al. |
| 2016/0184020 A1 | 6/2016 | Kowalewski et al. |
| 2016/0184021 A1 | 6/2016 | Kowalewski et al. |

FOREIGN PATENT DOCUMENTS

| | | |
|---|---|---|
| GB | 2208807 A | 4/1989 |
| WO | 1998019614 A1 | 5/1998 |
| WO | 2007115152 A2 | 10/2007 |
| WO | 2010042249 A4 | 8/2010 |

OTHER PUBLICATIONS

Moscato et al. A Micromachined Intensity-Modulated Fiber Optic Sensor for Strain Measurements: Working Principle and Static Calibration; 34th Annual International Conference of the IEEE EMBS, 2012, pp. 5790-5793.

Mujat et al.; Automated Algorithm for Breast Tissue Differentiation in Optical Coherence Tomogrpahy; Journal of Biomedical Optics 14(3), 2009, 9 pages.

Neuzil et al. Pacemaker and ICD Lead Extraction With Electrosurgical Dissection Sheaths and Standard Transvenous Extraction Systems: Results of a Randomized Trial; Europace 9 , 2007, pp. 98-104.

Nikonovas et al. The Application of Force-Sensing Resistor Sensors for Measuring Forces Developed by the Human Hand; Proc. Instn Mech Engrs. vol. 218 Part H, 2004, 9 pages.

Nilsson et al Near Infrared Diffuse Reflection and Laser-Induced Fluorescence Spectroscopy for Myocardial Tissue Characterization; Spectrochimica Acta Part A 53, 1997, pp. 1901-1912.

Noble et al. High Energy Excimer Laser to Treat Coronary In-Stent Restenosis in an Under Expanded Stent; Catheter and Cardiovascular Interventions vol. 71, 2008, pp. 803-807.

Noonan et al. A Dual-Function Wheeled Probe for Tissue Viscoelastic Property Identification During Minimally Invasive Surgery; IEEE International Conference on Robotics and Automation, Apr. 10-14, 2007, 6 pages.

Notice of Allowance for U.S. Appl. No. 12/649,759 dated May 16, 2013, 12 pages.

Notice of Allowance for U.S. Appl. No. 11/228,845 dated Jun. 5, 2009, 8 pages.

Notice of Allowance for U.S. Appl. No. 12/406,807 dated Aug. 2, 2010, 7 pages.

Notice of Alowance for U.S. Appl. No. 12/337,232 dated Sep. 6, 2013, 11 pages.

Official Action for U.S. Appl. No. 11/228,845 dated Jan. 12, 2009, 13 pages.

Official Action for U.S. Appl. No. 11/228,845 dated Sep. 3, 2008, 10 pages.

Official Action for U.S. Appl. No. 12/337,232 dated Mar. 23, 2012, 9 pages.

Official Action for U.S. Appl. No. 12/337,232 dated Sep. 13, 2012, 10 pages.

Official Action for U.S. Appl. No. 12/649,759 dated Aug. 30, 2012, 11 pages.

Official Action for U.S. Appl. No. 12/649,759 dated Jul. 16, 2012, 9 pages. (Restriction Requirement).

Okumura et al. A Systematic Analysis of in Vivo Contact Forces on Virtual Catheter Tip/Tissue Surface Contact During Cardiac Mapping and Intervention; J. Cardiovasc Electrophysiol, vol. 19, Jun. 2008, pp. 632-640.

Orengo et al. Characterization of Piezoresistive Sensors for Goniometric Glove in Hand Prostheses; Wireless VITAE, 2009 pp. 684-687.

Park et al. Exoskeletal Force-Sensing End-Effectors With Embedded Optical Fiber-Bragg Grating Sensors; IEEE Transactions on Robotics, vol. 25, No. 6, Dec. 2009, pp. 1319-1331.

Park et al. Fingertip Force Control With Embedded Fiber Bragg Grating Sensors; IEEE conference on Robotics and Automation, May 19-23, 2008, pp. 3431-3436.

Park et al. Force Sensing Robot Fingers Using Embedded Fiber Bragg Grating Sensors and Shape Deposition Manufacturing; ; IEEE International Conference on Robotics and Automation, Apr. 10-14, 2007, . pp. 1510-1516.

Parker et al. Advanced Imaging Catheter Gives Surgeons the Inside Picture; Brochure Jun. 12, 2013: https//www.llnl.gov/str/DaSilva.html.

Patterson et al. Time Resolved Reflectance and Transmittance for the Non-Invasive Measurement of Tissue Optical Properties; Applied Optics vol. 28, No. 12, Jun. 15, 1989 pp. 2331-2336.

Peracchia Surgical Education in the Third Millennium; Annuals of Surgery, vol. 234, No. 6. 2001. pp. 709-712.

Pettit et al. Dynamic Optical Properties of Collagen-Based Tissue During ARF Excimer Laser Oblation; Applied Optics vol. 32, No. 4 Feb. 1, 1993, pp. 488-493.

Piers et al. A Micro Optical Force Sensor for Force Feedback During Minimally Invasive Robotic Surgery; Elsevier Sensors and Actuators A 115, 2004, pp. 447-455.

Polygerinos et al. MRI-Compatible Fiber-Optic Force Sensors for Catheterization Procedures; IEEE Sensors Journal vol. 10 No. 10, Oct. 2010, pp. 1598-1608.

(56) References Cited

OTHER PUBLICATIONS

Post et al.; Outcome After Complete Percutaneous Removal of Infected Pacemaker Systems and Implantable Cardiac Defibrillators; Internal Medicine Journal 36, 2006, pp. 790-792.
Prasad et al. A Modular 2-DOF Force-Sensing Instrument for Laparoscopic Surgery; MICCAI 2003, LNCS 2878 pp. 279-286.
Puangmali et al. State-Of-The Art in Force and Tactile Sensing for Minimally Invasive Surgery; IEEE Sensors Journal vol. 8, No. 4, Apr. 2008, pp. 371-381.
Rajan et al. Photonic Crystal Fiber Sensors for Minimally Invasive Surgical Devices; IEEE Transactions on Biomedical Engineering, vol. 59, No. 2, Feb. 2012, pp. 332-338.
Reiley et al. Review of Methods for Objective Surgical Skill Evaluation Surg Endosc, vol. 25, 2011 pp. 356-366.
Richards et al. Skills Evaluation in Minimally Invasive Surgery Using Force/Torque Signatures; Surg Endosc vol. 14, 2000, pp. 791-798.
Rinaldi et al. Determinants of Procedural Outcome of Chronically Implanted Pacemaker and Defibrillator Leads Using the Excimer Laser Sheath Heart.bmj.com, Dec. 5, 2012, 3 pages.
Rocha et al. Fluorescence and Reflectance Spectroscopy for Identification of Atherosclerosis in Human Carotid Arteries Using Principal Components Analysis; Photomedicine and Laser Surgery vol. 26, No. 4, 2008, pp. 329-335.
Rosen et al. Markov Modeling of Minimally Invasive Surgery Based on Tool/Tissue Interaction and Force/Torque Signatures for Evaluating Surgical Skills; IEEE Transactions on Biomedical Engineering, vol. 48, No. 5 May 2001, 13 pages.
Rovithakis Artificial Neural Networks for Discriminating Pathologic From Normal Peripheral Vascular Tissue; IEEE Transactions on Biomedical Engineering, vol. 48, No. 10, Oct. 2001 pp. 1088-1097.
Ruttmann et al. Transvenous Pacemaker Lead Removal Is Safe and Effective Even in Large Vegetations: An Analysis of 53 Cases of Pacemaker Lead Endocarditis; Pace vol. 26, Mar. 2006 pp. 231-236.
Sangpradit et al. Tissue Identification Using Inverse Finite Element Analysis of Rolling Indentation; 2009 IEEE International Conference on Robotics and Automation; Kobe, Japan, May 12, 17, 2009, 6 pages.
Schroeder et al. Visualizing Surgical Training Databases: Exploratory Visualization, Data Modeling, and Formative Feedback for Improving Skill Acquisition: IEEE Computer Graphics and Applications, 2011, 11 pages; DOI 10.1109/MCG.2012.67.
Seibold et al. Prototype of Instrument for Minimally Invasive Surgery With 6-Axis Force Sensing Capability ; Proceedings of the 2005 IEEE International Conference on Robotics and Automation, Apr. 2005, 6 pages.
Sensor-Response-Compressive Force versus CNT sensor readout Chart, 2 pages.
Shah et al. Evaluation of a New Catheter Sensor for Real-Time Measurement of Tissue Contact; Heart Rhythm, vol. 3, No. 5, Supplement, May 2006 pp. S75-S76.
Simone et al. A Low Cost Instrumented Glove for Extended Monitoring and Functional Hand Assessment; Journal of Neuroscience Methods 160, 2007 pp. 335-348.
Smith et al. Extraction of Transvenous Pacing and ICD Leads; Pace vol. 31 Jun. 2008 pp. 736-752.
Sohail et al. Management and Outcome of Permanent Pacemaker and Implantable Cardioverter-Defibrillator Infections; Journal of the American College of Cardiology, vol. 49, No. 18, 2007 pp. 1851-1859.
Sokollik et al. New Model for Skills Assessment and Training Progress in Minimally Invasive Surgery; Surg Endosc vol. 18, 2004, pp. 495-500.
Sosa et al. The Importance of Surgeon Experience for Clinical and Economic Outcomes From Thyroidectomy; Annals of Surgery vol. 228, No. 3 pp. 320-330.
Final Official Action for U.S. Appl. No. 12/337,232 dated Apr. 23, 2013, 11 pages.

Fung et al. A PMMA-Based Micro Pressure Sensor Chip Using Carbon Nanotubes As Sensing Elements; IEEE International Conference on Micro Electro Mechanical Systems, vol. 18, 2005 pp. 251-254.
Ghosh et al. Laser Lead Extraction: Is There a Learning Curve?; Pace, vol. 28; Mar. 2005 pp. 180-184.
Golzio et al. Prevention and Treatment of Lead Extraction Complications; Transvenous Lead Extraction; Springer-Verlag Italia 2011 pp. 129-136.
Griffin et al. Calibration and Mapping of a Human Hand for Dexterous Telemanipulation; ASME IMECE Conference, 2000, 8 pages.
Grundfest, Warren S., MD, et al., "Laser Ablation of Human Atherosclerotic Plaque Without Adjacent Tissue Injury," JACC vol. 5, No. 4, (Apr. 1985), pp. 929-933.
Hager-Ross et al. Quantifying the Independence of Human Finger Movements: Comparisons of Digits, Hands, and Movement Frequencies; The Journal of Neurosciences, vol. 20 No. 22, Nov. 15, 2000, pp. 8542-8550.
Hajjarian et al. Intravascular Laser Speckle Imaging Catheter for the Mechanical Evaluation of the Arterial Wall; Journal of Biomedical Optics vol. 16(2) Feb. 2011, 7 pages.
Hanke et al. Morphological Changes and Smooth Muscle Cell Proliferation After Experimental Excimer Laser Treatment; Circulation vol. 83, 1991 pp. 1380-1389.
Hattori et al. Invivo Raman Study of the Living Rat Esophagus and Stomach Using a Micro-Raman Probe Under an Endoscope; Applied Spectroscopy vol. 61, No. 6, 2007, 8 pages.
Hauser Deaths and Cardiovascular Injuries Due to Device-Assisted Implantable Cardioverter-Defibrillator and Pacemaker Lead Extraction; Eurospace vol. 12, 2010, pp. 395-401.
Henning et al. An in Vivo Strain Gage Study of Elongation of the Anterior Cruciate Ligament; The American Journal of Sports Medicine, vol. 13, No. 1m 1985, pp. 22-26.
Inmann et al. An Instrument Object for Evaluation of Lateral Hand Grasp During Functional Tasks; Journal of Medical Engineering & Technology, vol. 25. No. 5, Sep./Oct. 2001, pp. 207-211.
Insull The Pathology of Atherosclerosis; Plaque Development and Plaque Responses to Medical Treatment; The American Journal of Medicine, vol. 122, No. 1A, Jan. 2009, 12 pages.
Interlink Electronics. State-of-the-Art Pointing Solutions for the OEM-FSR Force Sensing Resistor Integration Guide and Evaluation Parts Catalog: 400 Series Evaluation Parts With Suggested Electrical Interfaces. Interlink Electronics, Version 1.0 (90-45632 Rev. D), Camarillo, CA, pp. 1-26.
International Preliminary Report on Patentability issued in PCT/US2009/066133, dated Jun. 21, 2011, 8 pages.
International Preliminary Report on Patentability issued in PCT/US2014/019278, dated Sep. 24, 2015, 10 pages.
International Preliminary Report on Patentability issued in PCT/US2014/019283, dated Sep. 24, 2015, 10 pages.
International Search Report and Written Opinion issued in PCT/2014/019258, dated Aug. 8, 2014, 21 pages.
International Search Report and Written Opinion issued in PCT/2014/019283, dated Jun. 20, 2014, 15 pages.
International Search Report and Written Opinion issued in PCT/2014019278, dated May 7, 2014, 14 pages.
International Search Report and Written Opinion issued in PCT/US2005/033029, dated Oct. 3, 2006, 1 page.
International Search Report and Written Opinion issued in PCT/US2009/066133, dated Jan. 26, 2010, 8 pages.
Jagsi et al. Original Investigation: Residents Report on Adverse Events and Their Causes; Arch Intern Med/ vol. 163 Dec 12/26, 2005 7 pages.
Johns et al. Determination of Reduced Scattering Coefficient of Biological Tissue From a Needle-Like Probe; Optics Express vol. 13, No. 13. Jun. 27, 2005 pp. 4828-4842.
Kahol, K. et al. Effect of Fatigue on Psychomotor and Cognitive Skills. The American Journal of Surgery: Association for Surgical Education, 195:195-204, 2008.
Kane et al. A Traction Stress Sensor Array for Use in High-Resolution Robotic Tactile Imaging; Journal of Microelectromechanical Systems, vol. 9, No. 4, Dec. 2000, pp. 425-434.

(56) References Cited

OTHER PUBLICATIONS

Kang et al. A Carbon Nanotube Strain Sensor for Structural Health Monitoring; Smart Matter. Struct. vol. 15, 2006, pp. 737-748.
Karimov et al. A Carbon Nanotube-Based Pressure Sensor, Phys. Scr. 83, 2011, 5 pages.
Karsch et al. Percutaneous Coronary Excimer Laser Angioplasty Initial Clinical Results; The Lancet, Sep. 16, 1989 pp. 647-650.
Kennergren Excimer Laser Assisted Extraction of Permanent Pacemaker and ICD Leads: Present Experiences of a European Multi-Centre Study; European Journal of Cardio-Thoracic Surgery 15, 1990, pp. 856-860.
Khairy et al. Laser Lead Extraction in Adult Congenital Heart Disease; J. Cardiovasc Electrophysiol, vol. 18, 2006, pp. 507-511.
Khalil et al. Tissue Elasticity Estimation With Optical Coherence Elastography: Toward Mechanical Characterization of in Vivo Soft Tissue; Annals of Biomedical Engineering, vol. 33, No. 11, Nov. 2005, pp. 1631-1639.
Kochiadakis et al. The Role of Laser-Induced Fluorescence in Myocardial Tissue Characterization: An Experimental Invitro Study; Chest vol. 120, 2001, pp. 233-239.
Koulouris et al. Intravascular Lead Extractions: Tips and Tricks; Intech Open Science/Open Minds http//creativecommons.org/licenses/by/3.0, 2012 pp. 189-216.
Kremers et al. The National ICD Registry Report: Version 2.1 Including Leads and Pediatrics for Years 2010 and 2011; pp. 59-65.
Lathan et al. The Effects of Operator Spatial Perception and Sensory Feedback on Human-Robot Teleoperation Performance; Presence, vol. 11, No. 4, Aug. 2002, 368-377.
Levine et al. 2011 ACCF/AHA/SCAI Guideline for Percutaneous Coronary Intervention: Executive Summary; Journal of the American College of Cardiology vol. 58, No. 24, 2011, pp. 2250-2583.
Li et al. Strain and Pressure Sensing Using Single-Walled Carbon Nanotubes; Nanotechnology vol. 15, 2004, pp. 1493-1496.
Lieber et al. Sarcomere Length Determination Using Laser Diffraction: Effect of Beam and Fiber Diameter; Biophys J. vol. 45, May 1984, pp. 1007-1016.
Lipomi et al. Skin-Like Pressure and Strain Sensors Based on Transparent Elastic Films of Carbon Nanotubes; Nature Nanotechnology, vol. 6, Dec. 2011, pp. 788-792.
Maréchal, L. et al. "Measurement System for Gesture Characterization During Chest Physiotherapy Act on Newborn Babies Suffering from Bronchiolitis." Proceedings of the 29th Annual International Conference of the IEEE EMBS, Cité Internationale, Lyon, France. Aug. 23-26, 2007. pp. 5770-5773.
Maytin et al. Multicenter Experience With Extraction of the Sprint Fidelis Implantable Cardioverter-Defibrillator Lead; Journal of the American College of Cardiology vol. 56, No. 8, 2010, pp. 642-646.
Maytin et al. The Challenges of Transvenous Lead Extraction; Heart vol. 97, 2011, pp. 425-434.
Medtronic's Brochure; Implantable Pacemaker and Defibrillator Information; Apr. 2006, 2 pages.
Meier-Ewert et al. Endocardial Pacemaker or Defibrillator Leads With Infected Vegetations: A Single-Center Experience and Consequences of Transvenous Extraction; AM Heart Journal vol. 146, 2003, pp. 339-344/.
Menciassi et al. Force Sensing Microinstrument for Measuring Tissue Properties and Pulse in Microsurgery, IEEE/ASME Transactions on Mechatronics, vol. 8, No. 1, Mar. 2003, pp. 10-17.
Mishra et al. Fiber Grating Sensors in Medicine: Current and Emerging Applications; Sensors and Actualtors A, 167, 2011, pp. 279-290.
Missinne Flexible Miniature Shear Sensors for Prosthetics; SPIE Newsroom SPIE, May 13, 2013, 4 pages.
Missinne, Jeroen et al. "Embedded Flexible Optical Shear Sensor." IEEE Sensors 2010 Conference. 2010. pp. 987-990.
Abeysinghe et. Al. A Novel MEMS Pressure Sensor Fabricated on an Optical Fiber; IEEE Photonics Technology Letters vol. 13. No. 9 Sep. 2001 pp. 993-995.
Advisory Action for U.S. Appl. No. 12/337,232 dated Aug. 8, 2013, 3 pages.

Advisory Action issued in U.S. Appl. No. 12/337,232, dated Aug. 8, 2013, 3 pages.
Agency for Healthcare Research and Quality Adjunctive Devices in PCI to Remove Thrombi or Protect Against Distal Embolization in Patients With ACS: A Clinician Research Summary; Effective Health Care Program; AHRQ Pub. No. 11 (12)-EHC089-May 3, 2012 4 pages.
Arifler et. Al. Light Scattering From Collagen Fiber Networks: Micro-Optical Properties of Normal and Neoplastic Stroma; Biophysical Journal vol. 92 May 2007, pp. 3260-3274.
Ashok et al. Raman Spectroscopy Sensor for Surgical Robotics—Instrumentation and Tissue Differentiation Algorithm Biomedical Optics and 3D Imaging OSA 2012 4 pages.
Bach et al., Design and Fabrication of 60-Gb/s InP-Based Monolithic Photoreceiver OEICs and Modules, IEEE Journal of Selected Topics in Quantum Electronics, vol. 8, No. 6, Nov. 1, 2002, 6 pgs.
Baddour et al. Update on Cardiovascular Implantation Electronic Device Infections and Their Management: A Scientific Statement From the American Heart Association Circulation 121: Jan. 2010, pp. 458-477.
Badr et al. The State of the Excimer Laser for Coronary Intervention in the Drug-Eluting Stent ERA Cardiovascular Revascularization Medicine 14, 2013, pp. 93-98.
Bann et al. Attitudes Towards Skills Examinations for Basic Surgical Trainees J. Clin Pract Jan. 2005, 59, 1. pp. 107-113.
Baztarrica et al. Transvenous Extraction of Pacemaker Leads in Infective Endocarditis With Vegetations ≥20MM: Our Experience; Clinl. Cardiol 35, 4, 2012 pp. 244-249.
Beauvoit et al. Contribution of the Mitochondrial Compartment to the Optical Properties of the Rat Liver: A Theoretical and Practical Approach Biophysical Journal vol. 67 Dec. 1994 pp. 2501-2510.
Beccai et al. Design and Fabrication of a Hybrid Silicon Three-Axial Force Sensor for Biomechanical Applications; Sensors and Actuators A 120, 2005, pp. 370-382.
Berkelman et al. A Miniature Microsurgical Instrument Tip Force Sensor for Enhanced Force Feedback During Robot-Assisted Manipulation; IEEE Transactions on Robotics and Automaton, vol. 19, No. 5, Oct. 2003, pp. 917-922.
Bilodeau et al. Novel Use of a High-Energy Excimer Laser Catheter for Calcified and Complex Coronary Artery Lesions Catheterization and Cardiovascular Interventions 62: 2004 pp. 155-161.
Bindig et al. Fiber-Optical and Microscopic Detection of Malignant Tissue by Use of Infrared Spectrometry Journal of Biomedical Optics vol. 7 No. 1 Jan. 2002 pp. 100-108.
Bishop et al. Paid Malpractice Claims for Adverse Events in Inpatient and Outpatient Settings; JAMA vol. 205 No. 23 Jun. 15, 2011, pp. 2427-2431.
Bittl et al. Meta-Analysis of Randomized Trials of Percutaneous Transluminal Coronary Angioplasty Versus Atherectomy, Cutting Balloon Atherotomy, or Laser Angioplasty Journal of the American College of Cardiology vol. 43 No. 6 2004 pp. 936-942.
Bongiorni et al. Transvenous Removal of Pacing and Implantable Cardiac Defibrillating Leads Using Single Sheath Mechanical Dilatation and Multiple Venous Approaches; High Success Rate and Safety in More Than 200 Leads; European Heart Journal vol. 29, 2008, pp. 2886-2893.
Bracke et al. Pacemaker Lead Complications: When Is Extraction Appropriate and What Can We Learn From Published Data? Heart 2001 vol. 85 pp. 254-259.
Brennan et al. Analysis of Errors Reported by Surgeons at Three Teaching Hospitals, Surgery vol. 3, No. 6, 2003 pp. 614-621.
Britton Chance Optical Method; Annu Rev. Biophys. Chem vol. 20 1991 pp. 1-30.
Buch et al. Pacemaker and Defibrillator Lead Extraction; Circulation 2011:123 pp. 378-380.
Byrd et al. Clinical Study of the Laser Sheath for Lead Extraction: The Total Experience in the United States; Journal of Pacing and Clinical Electrophysiology, vol. 25 No. 5, May 2002 pp. 804-808.
Byrd et al. Intravascular Lead Extraction Using Locking Stylets and Sheaths; Pace vol. 13 Dec. 1990, pp. 1871-1875.
Candefjord et al. Combining Fibre Optic Raman Spectroscopy and Tactile Resonance Measurement for Tissue Characterization; Meas. Sci Technol. vol. 21, 2010 125801 8 pages.

(56) References Cited

OTHER PUBLICATIONS

Candinas et al. Postmortem Analysis of Encapsulation Around Long-Term Ventricular Endocardial Pacing Leads; Mayo Clin Proc. vol. 74, Feb. 1999, pp. 120-125.
Carlson et al. Motion Capture Measures Variability in Laryngoscopic Movement During Endotracheal Intubation: A Preliminary Report; 2012 Society for Simulation in Healthcare, vol. 7, No. 1, Aug. 2012 pp. 255-260.
Chan et al. Effects of Compression on Soft Tissue Optical Properties; IEEE Journal of Selected Topics in Quantum Electronics, vol. 2 No. 4, Dec. 1996 pp. 943-950.
Cheong et al. A Review of the Optical Properties of Biological Tissues; IEEE Journal of Quantum Electronics vol. 26, No. 12, Dec. 1990 pp. 2166-2185.
Chung, Kit Man. Advanced Fibre Bragg Grating and Microfibre Bragg Grating Fabrication Techniques; A Thesis Submitted in Partial Fulfillment of the Requirements for the Degree of Doctor of Philosophy the Hong Kong Polytechnic University; Mar. 2012 (abstract of thesis/document attached; full printed version of thesis/document unavailable; entire online version of thesis/document available at http://repository.lib.polyu.edu.hk/jspui/handle/10397/5524).
Cruz et al. Internal Mammary Arterial Injury From Lead Extraction: A Clinically Subtle Yet Important Complication of Implantable Device Removal; Cardiology Research and Practice vol. 2011, Article ID 408640, (2011) 5 pages.
Da et al. Overview of the Vascular Interventional Robot; The International Journal of Medical Robotics and computer assisted surgery 2008;4: pp. 289-294.
Dallon et al. A Mathematical Model for Spatially Varying Extracellular Matrix Alighment; Siam J. Appl. Math. vol. 61, No. 2, 2000, pp. 506-527.
Deharo et al. Pathways for Training and Accreditation for Transvenous Lead Extraction: A European Heart Rhythm Association Position Paper; Europace 14 (2012) pp. 124-134.
Dipietro et al. Evaluaton of an Instrumented Glove for Hand-Movement Acquisition; Journal of Rehabilitation Research and Development vol. 40, No. 2, Mar./Apr. 2003, pp. 179-190.
Eichhorn et al. Carbon Nanotube Filled Composite Material Analysis Utilizing Nano and Conventional Testing Techniques; NIP & Digital Fabrication Conference, 2010 International Conference on Digital Printing Technologies. 5 Pages.
Eichhorn et al. Flexible Carbon Nanotube Composite Sensors for Medical Device Application; J. Med. Devices 7(2), 020943 (Jun. 11, 2013) (2 pages)Paper No. MED-13-1050; doi: 10.1115/1.4024311.
ELCA Coronary Laser Atherectomy Catheter Brochure, Spectranetics, 2012.
El-Sawah et al. A Prototype for 3-D Hand Tracking and Posture Estimation; IEEE Transactions on Instrumentation and Measurement, vol. 57, No. 8, Aug. 2008, pp. 1627-1636.
Endo et al. Clinical Utility of Intraprocedural Transesophagael Echocardiography During Transvenous Lead Extraction; Journal of the American Society of Echocardiography vol. 21 No. 7, Jul. 2008 pp. 862-867.
Epstein et al. Gross and Microscopic Pathological Changes Associated With Nonthoracotomy Implantable Defibrillator Lead; Circulation 1998;98: 1517-1524.
Erturk et al. Outcome of Surgery for Acromegaly Performed by Different Surgeons: Importance of Surgical Experience; Pituitary 8: 2005, pp. 93-97.
Esenaliev, O. R., et al. Laser Ablation of Atherosclerotic Blood Vessel Tissue Under Various Irradiation Conditions. IEEE Transactions on Biomedical Engineering, 36(12):1188-1194, Dec. 1989.
Esposito et al. Morphologic and Immunohistochemical Observations of Tissues Surrounding Retrieved Transvenous Pacemaker Leads; Wiley Periodicals, Inc. 2002, pp. 548-558.
European Search Report issued in EP Application No. 05796879.4 dated Mar. 6, 2008, 7 pages.
European Search Report issued in EP Application No. 08010688.3. dated Feb. 17, 2009, 6 pages.

Faber et al. Light Absorption of (Oxy-) Hemoglobin Assessed by Spectroscopic Optical Coherence Tomography; Optics Letters vol. 28, No. 16, Aug. 15, 2003 pp. 1436-1438.
Fanson et al. A System for Laparoscopic Surgery Ergonomics and Skills Evaluation; Journal of Endourology vol. 25, No. 7, Jul. 2011 pp. 1111-1114.
U.S. Appl. No. 09/947,171, filed Sep. 4, 2001, 71 pages.
Spectranetics User Manual VisiSheath Dilator Sheath, 2011, 112 Pages.
Spectranetics X80 User Manual ELCA Coronary Laser Atherectomy Catheter. Mar. 2012, 16 pages.
Spectranetics. ELCA Coronary Laser Atherectomy Catheter: Instructions for Use, 0.9 mm OTW and 0.9 mm RX X-80 Catheter Models, Mar. 14, 2012, pp. 1-16.
SPI2006 Shear Sensor Brochure—Real-Time Surface Shear Sensing Application: Human Interface; Tactilus Technology, 2006, 1 page.
Sturman et al. A Survey of Glove-Based Input; Clumsy Intermediary Devices Constrain Our Interaction With Computers and Their Applications. Glove-Based Input Devices Let Us Apply Our Manual Dexterity to the Task: IEEE Computer Graphics & Applications, Jan. 1994. pp. 30-39.
Sun et al. A Sub-Millemetric, 0.25 Mn Resolution Fully Integrated Fiber-Optic Force Sensing Tool for Retinal Microsurgery; Int J Comput Assist Radiol Surg. vol. 4(4): Jun. 2009, pp. 383-390.
Takano et al. Changes in Coronary Plaque Color and Morphology by Lipid-Lowering Therapy With Atorvastatin: Serial Evaluation by Coronary Angioscopy; The Journal of the American College of Cardiology, vol. 42, No. 4, 2003 pp. 680-686.
Taroni et al. In Vivo Absorption and Scattering Spectroscopy of Biological Tissues; Photochem. Photobiol. Sci. vol. 2, 2003. pp. 124-129.
Turchin et al. Novel Algorithm of Processing Optical Coherence Tomography Images for Differentiation of Biological Tissue Pathologies; Journal of Biomedical Optics 10(6), Nov./Dec. 2005, 11 pages.
Turner et al. Development and Testing of a Telemanipulation System With Arm and Hand Motion; Accepted to 2000 ASME IMECE Symp. Haptic Interfaces, 2000, 7 pages.
U.S. Appl. No. 14/586,312, filed Dec. 30, 2014.
U.S. Appl. No. 14/586,529, filed Dec. 30, 2014.
U.S. Appl. No. 14/586,543, filed Dec. 30, 2014.
Valdastri et al. Integration of a Miniaturized Triaxial Force Sensor in a Minimally Invasive Surgical Tool; IEEE Transactions on Biomedical Engineering, vol. 53, No. 11, Nov. 2006 pp. 2397-2400.
Van der Meer et al. Quantitative Optical Coherence Tomography of Arterial Wall Components; Lasers in Medical Science vol. 20, 2005, pp. 45-51.
Van der Meijden et al. The Valve of Haptic Feedback in Conventional and Robot-Assisted Minimal Invasive Surgery and Virtual Reality Training: A Current Review; Surg. Endosc vol. 23, 2009. pp. 1180-1190.
Van Leeuwen et al. Origin of Arterial Wall Dissections Induced by Pulsed Excimer and Mid-Infrared Laser Ablation in the PIGL; JACC vol. 19, No. 7, Jun. 1992, pp. 1610-1618.
Van Lindert et al. The Influence of Surgical Experience on the Rate of Intraoperative Aneurysm Rupture and Its Impact on Aneurysm Treatment Outcome; Surg Neurol vol. 56, 2001, pp. 151-158.
Wagner et al. The Role of Force Feedback in Surgery: Analysis of Blunt Dissection; Presented at the Tenth Symposium on Haptic Interfaces for Virtual Environment and Teleoperator Systems, Mar. 24, 25, 2002, 7 pages.
Walker et al. Surgical Safety Checklists: Do They Improve Outcomes?; British Journal of Anaesthesia, 2012, pp. 1-8.
Wang et al. Characterization of a Silicon=Based Shear-Force Sensor on Human Subjects; IEEE Trans Biomed Eng., 2002 1 page.
Wang et al. Miniature All-Silica Optical Fiber Pressure Sensor With an Ultrathin Uniform Diaphragm; Optics Express vol. 18, No. 9, Apr. 26, 2010 pp. 9006-9014.
Wang et al. Review: the Physiological and Computational Approaches for Atherosclerosis Treatment; IJCA-15372, 2012, 13 pages.
Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.

(56) References Cited

OTHER PUBLICATIONS

Wazni et al. Lead Extraction in the Contemporary Setting: The Lexicon Study; Journal of the American College of Cardiology vol. 55, No. 6, 2010, pp. 579-586.

Weiss et al. Muscular and Postural Synergies of the Human Hand; J. Neurophysiol 92, 2004pp. 523-535.

Wikipedia, Linear discriminant analysis, Dec. 21, 2013, http://en.wikipedia.org/wiki/Linear_discriminant_analysis.

Wilkoff et al. Transvenous Lead Extraction: Heart Rhythm Society Expert Consensus on Facilities, Training, Indications, and Patient Management; Heart Rhythm, vol. 6, No. 7, Jul. 2009, pp. 1086-1104.

Wise et al. Evaluation of a Fiber Optic Glove for Semi-Automated Goniometric Measurements; Journal of Rehabilitation Research and Development vol. 27 No. 4, 1990, pp. 411-424.

Wollmann et al. Two Different Therapeutic Strategies in ICD Lead Defects: Additional Combined Lead Versus Replacement of the Lead; Journal of Cardiovascular Electrophysiology vol. 18, No. 11, Nov. 2007, pp. 1172-1177.

Yamamoto et al. Tissue Property Estimation and Graphical Display for Teleoperated Robot-Assisted Surgery; 2009 IEEE International Conference on Robotics and Automation, May 12, 17, 2009, 7 pages.

Yokoyama et al. Novel Contact Force Sensor Incorporated in Irrigated Radiofrequency Ablation Catheter Predicts Lesion Size and Incidence of Steam Pop and Thrombus Clinical Perspective; Circulation Arrhythmia and electrophysiology: Journal of the American Heart Association, Dec. 2008, pp. 353-362.

Yun et al. An Instrumented Glove for Grasp Specification in Virtual-Reality-Based Point and Direct Telerobotics; IEEE Transactions on Systems, Man, and Cybernetics—Bart B: Cybernetics, vol. 27, No. 5, Oct. 1997, pp. 835-846.

Zhan et al. Excess Length of Stay, Charges, and Mortality Attributable to Medical Injuries During Hospitalization; Journal of American Medical Association, vol. 290, No. 14, Oct. 8, 2003, pp. 1868-1874.

\* cited by examiner

SYSTEM AND METHOD FOR COORDINATED LASER DELIVERY AND IMAGING

CROSS-REFERENCE TO RELATED APPLICATION

The present application is a continuation of U.S. patent application Ser. No. 14/723,956 filed May 28, 2015, entitled "SYSTEM AND METHOD FOR COORDINATED LASER DELIVERY AND IMAGING", which claims the benefit of and priority to, under 35 U.S.C. § 119(e), U.S. Provisional Application Ser. No. 62/004,666, filed May 29, 2014, entitled SYSTEM AND METHOD FOR SYNCHRONIZED LASER DELIVERY AND IMAGING, both of which are hereby incorporated by reference in their entirety for all purposes.

FIELD OF THE DISCLOSURE

The present disclosure relates generally to a method and system for delivering laser energy to and visualizing a target site, and more specifically to a method and system for coordinating output signals from an imaging source and a laser source.

BACKGROUND

Human blood vessels often become occluded or blocked by plaque, thrombi, other deposits, or emboli which reduce the blood carrying capacity of the vessel. If the blockage occurs at a critical place in the circulatory system, serious and permanent injury can occur. Medical intervention, such as an angioplasty or balloon dilation, is usually performed when significant occlusion is detected. For example, laser based catheter devices are often used to ablate the occlusions in the vessels (that is, perform atherectomy or removal of the stenosis).

Imaging technology is used to provide visualizations of surgical areas in the human body including vascular spaces. Standard fluoroscopy provides a two-dimensional (2D) view of the relative position and direction of a vascular space. Intravascular imaging technologies provide a visualization of the interior of vascular spaces and include, for example, intravascular ultrasound (IVUS), optical coherence tomography (OCT), and optical coherence reflectometry (OCR). When intravascular imaging technologies are used in conjunction with laser based ablation devices, the laser energy and vibration may cause interference with the imaging signal (e.g., ultrasound or light reflectance) of the intravascular imaging device.

SUMMARY

According to an exemplary embodiment of the present disclosure, a laser ablation and imaging system is provided including a laser source operative to provide a laser signal and an imaging source operative to provide an imaging signal. The laser signal and the imaging signal each include a plurality of pulses. The laser ablation and imaging system includes at least one delivery device operative to output the laser signal and the imaging signal to a target area. The laser ablation and imaging system further includes a controller in communication with the laser source and the imaging source. The controller is operative to coordinate the laser signal and the imaging signal such that each pulse of the laser signal and each pulse of the imaging signal are output in non-overlapping time windows.

According to an exemplary embodiment of the present disclosure, a laser ablation and imaging method is provided. The method includes activating an imaging source to provide a pulsed imaging signal. The method further includes activating a laser source to provide a pulsed laser signal while the imaging source remains activated. The method further includes coordinating the pulsed laser signal and the pulsed imaging signal to output each pulse of the pulsed laser signal and each pulse of the pulsed imaging signal in non-overlapping time windows.

According to another exemplary embodiment of the present disclosure, a non-transitory computer-readable medium containing certain instructions is provided. The non-transitory computer-readable medium contains instructions that, when executed, cause one or more processor to perform the following: activate an imaging source to provide a pulsed imaging signal; activate a laser source to provide a pulsed laser signal while the imaging source remains activated; and coordinate the pulsed laser signal and the pulsed imaging signal to output one or more laser pulses of the pulsed laser signal and one or more imaging pulses of the pulsed imaging signal in an asynchronous manner such that the one or more laser pulses and the one or more imaging pulses are emitted from a catheter in non-overlapping time windows.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter). A "laser catheter" is a catheter that includes optical fibers capable of transmitting laser light.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The term "logic" or ""control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion on and/or in conjunction with computer-readable medium and would remain in accordance with the embodiments herein disclosed.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

The term "coordinated" and variations thereof refer to controlling multiple signals such that pulses based on the signals (for example, laser pulses and imaging pulses) are output at certain times relative to each other type of signal. For example, laser pulses based on corresponding laser activation signals and imaging pulses based on corresponding imaging activation signals may be output in synchronized non-overlapping time windows or in an asynchronous manner.

A "laser emitter" refers to an end portion of a fiber or an optical component that emits laser light from a distal end of the catheter towards a desired target, which is typically tissue.

An optical fiber (or laser active fibre) is a flexible, transparent fiber made of an optically transmissive material, such as glass (silica) or plastic, which functions as a waveguide, or "light pipe", to transmit light between the two ends of the fiber.

Figure 1:
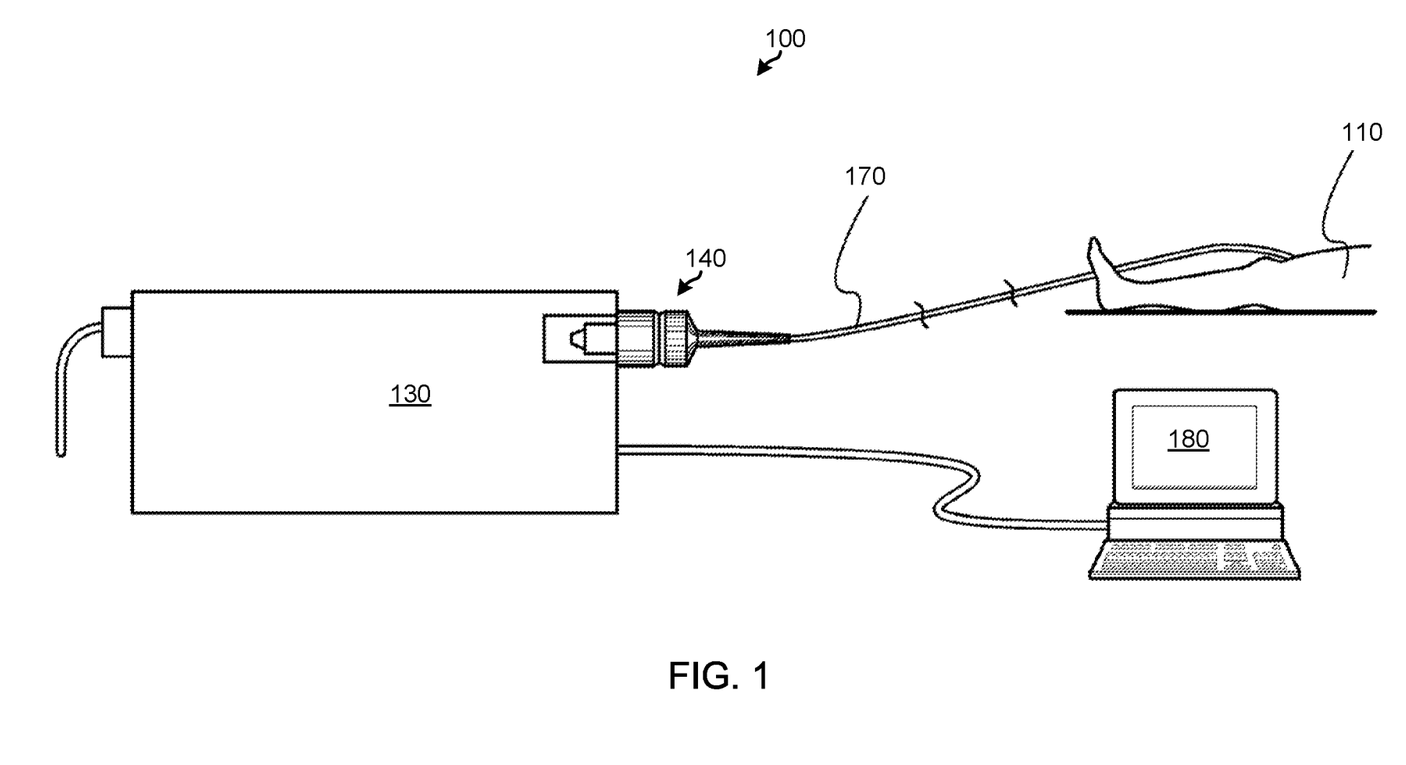
FIG. 1 illustrates a laser ablation and imaging system according to some embodiments of the present disclosure.

FIG. 1 illustrates a laser ablation and imaging system 100 according to some embodiments. Laser ablation and imaging system 100 includes a laser generator 130 coupled to a laser controller 180. Controller 180 includes one or more computing devices having computer readable medium programmed to control laser generator 130, as described herein with reference to FIGS. 3-5. Controller 180 may be internal or external to laser generator 130. Laser generator 130 may include an excimer laser or another suitable laser. In some embodiments, laser generator 130 produces light in the ultraviolet frequency range. Laser generator 130 is connected with the proximal end of a laser catheter 170 via coupler 140. The distal end of catheter 170 may be inserted into a vessel or tissue of a human body 110. In some embodiments, system 100 employs a plurality of light guides, such as optical fibers, that guide laser light from laser generator 130 through catheter 170 toward a target area in human body 110.

Figure 2A:
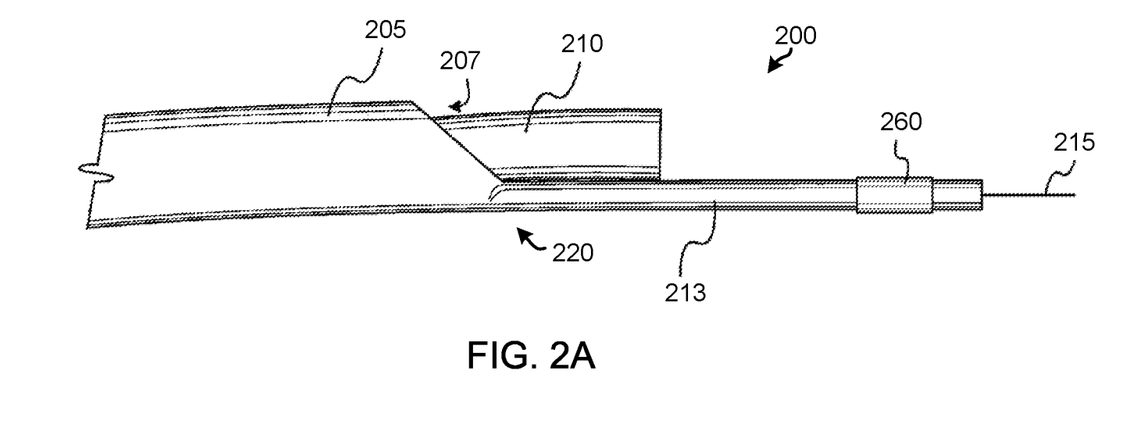
FIG. 2A illustrates an exemplary laser catheter of the laser ablation and imaging system of FIG. 1 including a distal imaging device.
Figure 2B:
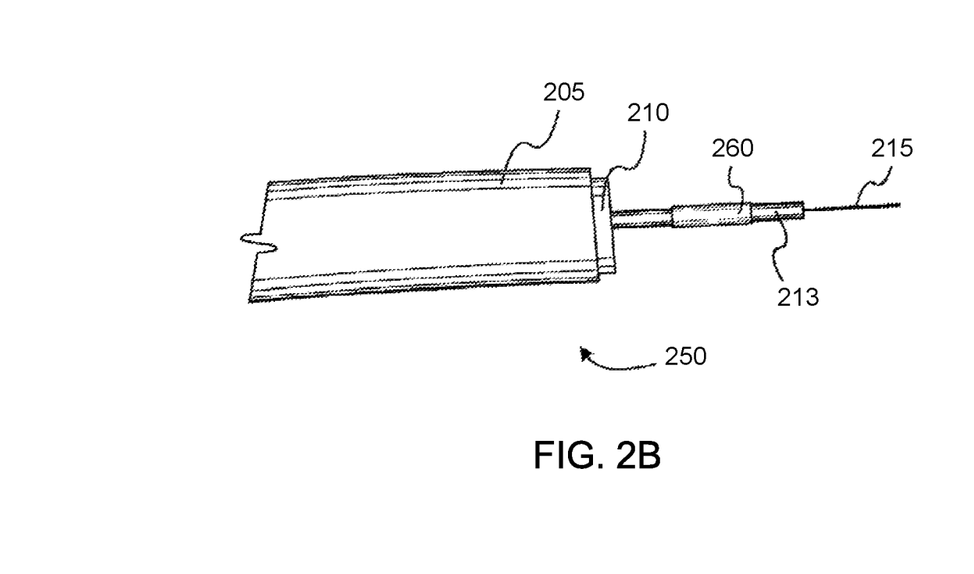
FIG. 2B illustrates another exemplary laser catheter of the laser ablation and imaging system of FIG. 1 including a distal imaging device.

Exemplary laser catheters 170 of FIG. 1 are illustrated in FIGS. 2A and 2B. Referring to FIGS. 2A and 2B, a laser catheter 200 (FIG. 2A) and a laser catheter 250 (FIG. 2B) each include a distal imaging device 260. Laser catheters 200 and 250 each illustratively include a catheter body 205 (or sheath) within which a fiber optic bundle 210 (or any other optical light guide) is disposed. Fiber optic bundle 210 includes any suitable number of optical fibers and, in some embodiments, includes a separate sheath. The optical fibers of bundle 210 serve as laser emitters at the distal end of bundle 210 by emitting pulsed laser energy to the targeted body lumen or tissue, such as a blood vessel, ureter, fallopian tube, cerebral artery. The pulsed laser energy serves to remove obstructions or other unwanted structures from the targeted lumen and/or tissue.

Catheter body 205 includes a distal end 220 and a proximal end opposite distal end 220. The proximal end of catheter body 205 includes coupler 140 (FIG. 1) that is configured to couple with laser generator 130 of FIG. 1. The proximal end of the fiber optic bundle 210 may also be coupled with coupler 140 in order to receive and conduct laser light provided with a laser source 310 (FIG. 3) through the optical fibers. Distal end 220 of catheter body 205 includes an opening 207 from which the distal end of fiber optic bundle 210 extends.

As illustrated in FIGS. 2A and 2B, imaging device 260 is disposed distal relative to the exit aperture of fiber optic bundle 210. In some embodiments, imaging device 260 is disposed on an eccentric or axially offset distal tip 213, as illustrated in FIG. 2A. In other embodiments, imaging device 260 is disposed on an axially centered distal tip 213 positioned in fiber optic bundle 210, as illustrated in FIG. 2B. In some embodiments, imaging device 260 is disposed distal relative to the exit aperture of light guide 210. In some embodiments, imaging device 260 is positioned between about 0.4 and 1.0 centimeters longitudinally (or forward) from the distal end (or exit aperture) of light guide 210, although other suitable positions of imaging device 260 may be provided. For example, the imaging device 260 may be disposed proximal relative to the exit aperture of light guide 210. That is, the light guide 210 may be disposed distal relative to the imaging device 260.

In one embodiment, imaging device 260 is an ultrasonic device, for example, such as an Intracoronary/Intravascular Ultrasound (ICUS/IVUS) device, which employs small transducers arranged on catheter 170 of FIG. 1. In the illustrated embodiment, imaging device 260 is driven by an imaging source 312 of FIG. 3 to output ultrasonic (or light reflectance) signals. Imaging device 260 further provides electronically transduced echo signals back to imaging source 312 and/or controller 180 (FIG. 3), and controller 180 produces a two or three-dimensional image of the target area such as the lumen, the arterial tissue, plaque, blockages, and/or tissue surrounding the artery. These images are generated in substantially real time and during the laser operation. An ultrasonic imaging device 260, for example, may include a flexible polyimide film layer. Imaging device 260 may alternatively use light reflectance signals or other suitable imaging signals to capture the image of the target area.

Figure 3:
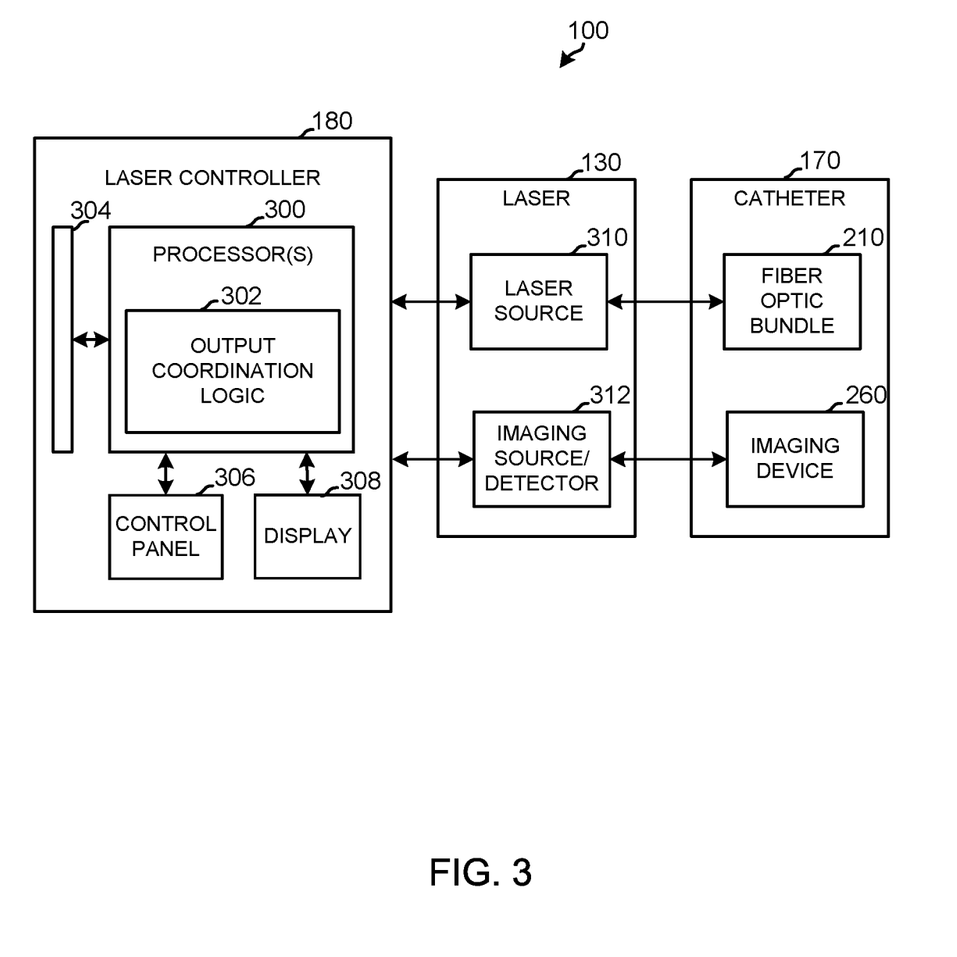
FIG. 3 illustrates a laser controller of the laser ablation and imaging system of FIG. 1 including output coordination logic that operates in conjunction with computer readable medium.

Imaging device 260 may be coupled with a number of wires and/or fiber optics that extend through catheter body 205 toward the proximal end of catheter 200, 250 for coupling with imaging source 312 (see FIG. 3). For example, for IVUS imaging devices, seven braided wires may be used. Some or all of these wires may have a diameter less than 0.01 inches, for example.

Referring to FIG. 3, laser controller 180 of FIG. 1 includes one or more processors 300 configured to execute instructions stored in memory 304 for controlling laser generator 130. Controller 180 includes a control panel 306 having one or more user input devices, such as keys or buttons, for example, providing user control of laser generator 130. A display 308 includes a monitor or other display device for displaying images from imaging device 260 and other laser operation data.

Laser source 310 of laser generator 130 is operative to generate a laser signal or beam and provide the laser signal through fiber optic bundle 210 of catheter 170 to the human. Imaging source 312 includes a signal generator for providing an imaging signal to imaging device 260, and imaging device 260 outputs the imaging signal. The imaging signal may include an ultrasonic signal or other suitable signal type. Imaging source 312 may be internal to laser generator 130 or may be physically separate from laser generator 130. In another embodiment, imaging source 312 is provided in imaging device 260 for generating and outputting the imaging signal. Fiber optic bundle 210 and imaging device 260 of catheter 170 serve as delivery devices for delivering the laser signal and imaging signal to the target area of the human.

Additional details of an exemplary laser generator 130 are described in U.S. Pat. No. 5,383,199, filed Jul. 2, 1992, entitled "Apparatus and Method for Optically Controlling the Output Energy of a Pulsed Laser Source," the entire disclosure of which is incorporated by reference herein. Additional details of exemplary catheters 170 are described in U.S. Pat. No. 8,545,488, filed Dec. 30, 2009, entitled "Cardiovascular Imaging System," the entire disclosure of which is incorporated by reference herein.

In the illustrated embodiment, laser source 310 and imaging source 312 output the respective laser and imaging signals as a plurality of pulses. Processor 300 of FIG. 3 includes output coordination logic 302 operative to coordinate the pulsed output of laser source 310 and imaging source 312. The pulsed signals from laser source 310 and imaging source 312 are coordinated by logic 302 of controller 180 to reduce or eliminate signal interference, as described herein.

Figure 4A:
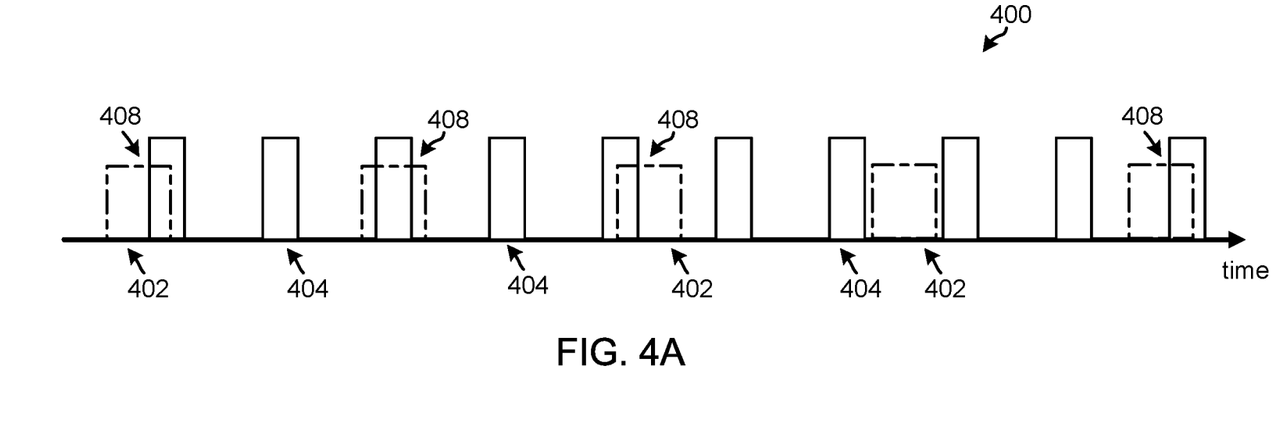
FIG. 4A illustrates exemplary non-coordinated laser and imaging signals.

FIG. 4A illustrates exemplary pulse trains 400 of a laser signal and an imaging signal in a non-coordinated laser and imaging system. Time is represented as the horizontal axis. Output pulses 402 of the laser signal are illustrated with dashed lines, and output pulses 404 of the imaging signal are illustrated with solid lines. The laser and imaging signals illustratively have different pulse frequencies. The simultaneous, non-coordinated output of the laser and imaging signals during an ablation procedure results in the laser pulses 402 overlapping, either entirely or partially, in time with the imaging pulses 404, as illustrated at interference areas 408 in the graph of FIG. 4A. With the signal delivery devices (imaging device 260 and fiber optic bundle 210 of FIG. 3) being positioned near each other at the distal end of the catheter 170 (see FIGS. 2A and 2B), such pulse interference may negatively affect the operation of the laser and imaging system, including potentially reducing the accuracy or effectiveness of the laser and the clarity of the captured images.

Figure 4B:
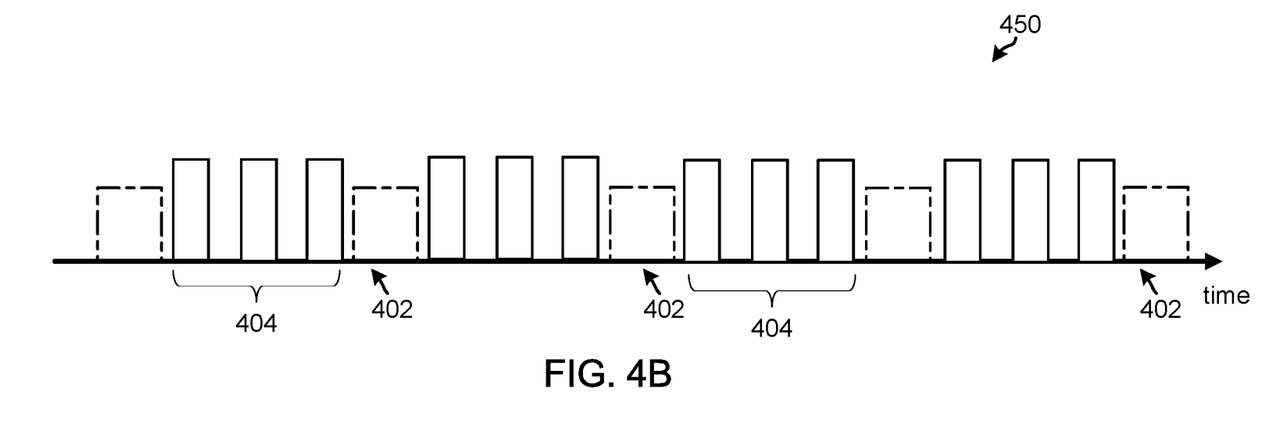
FIG. 4B illustrates exemplary coordinated laser and imaging signals output by the laser ablation and imaging system of FIGS. 1-3.

FIG. 4B illustrates exemplary pulse trains 450 of the laser signal and imaging signal output by laser ablation and imaging system 100 of FIG. 1 when coordinated by controller 180 of FIG. 3. Time is represented as the horizontal axis. The output pulses 402 of the laser signal are illustrated with dashed lines, and the output pulses 404 of the imaging signal are illustrated with solid lines. In the coordinated system 100, controller 180 controls laser source 310 and imaging source 312 of FIG. 3 to output laser pulses 402 and imaging pulses 404 in non-overlapping time windows to reduce or eliminate signal interference. In particular, imaging source 312 and imaging device 260 are controlled to output one or more imaging pulses 404 during the time period or window between each consecutive laser pulse 402 or pulses (not shown). In the illustrated embodiment, a plurality of imaging pulses 404 are output between each consecutive laser pulse 402, and the imaging pulses 404 are paused or delayed while each laser pulse 402 is output. Laser pulses 402 of FIG. 4B are illustratively output at the same frequency as the laser pulses 402 of the non-coordinated system illustrated in FIG. 4A, and the timing and frequency of the imaging pulses 404 of FIG. 4B are adjusted to avoid interference with laser pulses 402. The timing and frequency of laser pulses 402 may also be adjusted by coordination logic 302 to coordinate the laser and image signals. For example, the frequency of the laser pulses and the imaging pulses may be the same, but the duration (length), start time, end time of the laser pulses and the imaging pulses may be offset from one another so as to prevent overlap of the laser pulses and the imaging pulses.

Figure 5:
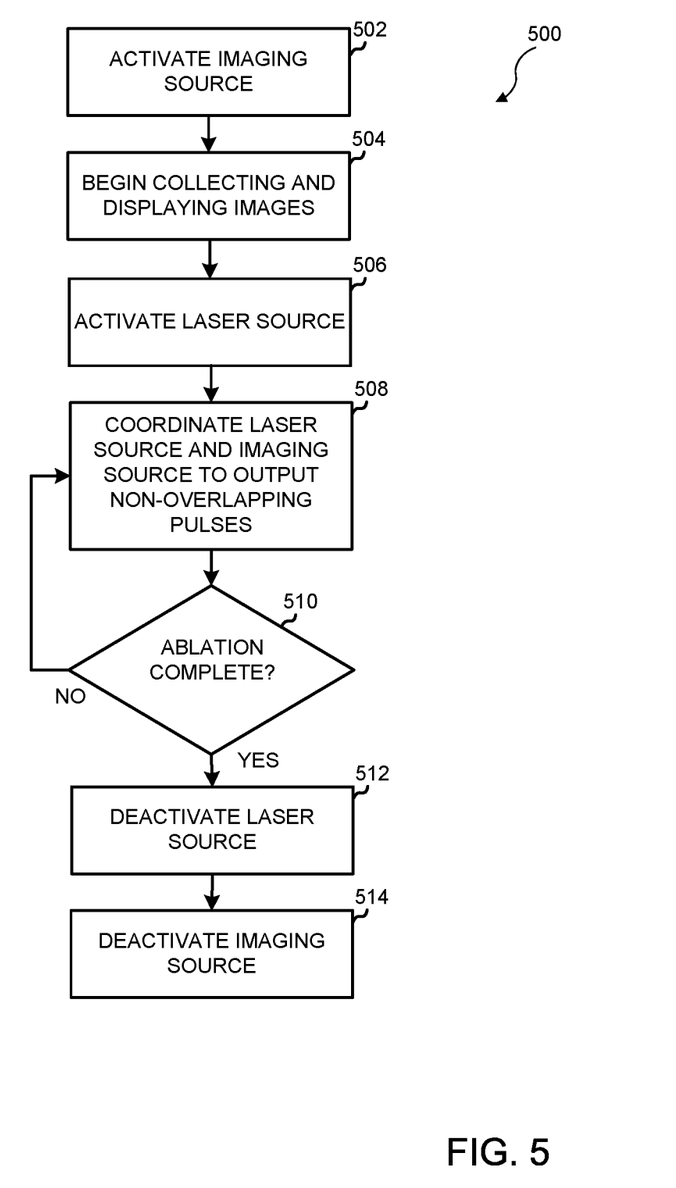
FIG. 5 illustrates a flow diagram of an exemplary method of controlling the laser ablation and imaging system of FIGS. 1-3.

FIG. 5 illustrates a flow diagram 500 of an exemplary method of operation of laser controller 180 of FIGS. 1 and 3. Reference is made to FIGS. 1-3 through the description of FIG. 5. At block 502, controller 180 activates imaging source 312 to output the imaging signal. Controller 180 begins collecting images with imaging device 260 and displaying the images on display 308 at block 504. At block 506, controller 180 activates laser source 310 to generate and output the pulsed laser signal for performing the laser ablation. In one embodiment, laser source 310 is activated in response to user input received via control panel 306. In one embodiment, imaging source 312 and laser source 310 are activated at substantially the same time. At block 508, coordination logic 302 of controller 180 coordinates operation of laser source 310 and imaging source 312 such that the pulses of the laser signal and imaging signal output by catheter 170 do not overlap in time, as described with respect to FIG. 4B. Controller 180 continues to coordinate the concurrent operation of laser source 310 and imaging source 312 until the laser ablation is complete at block 510. When the ablation procedure is complete (or stopped by the operator), controller 180 deactivates laser source 310 at block 512. At block 514, controller 180 deactivates imaging source 312 in response to user input or automatically after deactivating laser source 310.

As described herein, the imaging source 312 and imaging device 260 are enabled and capturing images throughout the laser ablation by laser generator 130. By coordinating the pulsed output signals of the laser source 310 and imaging source 312, signal interference is reduced or eliminated.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A laser ablation and imaging system including:
   a laser source operative to provide a laser signal, wherein an output of the laser signal comprises a plurality of laser pulses having a laser frequency;
   an imaging source operative to provide an imaging signal, wherein an output of the imaging signal comprises a plurality of imaging pulses forming a plurality of imaging series, wherein each of the imaging series comprises at least two of the imaging pulses, wherein each of the imaging series comprises an imaging series frequency, wherein the at least two of the imaging pulses within each imaging series comprise an imaging pulse frequency;
   at least one delivery device operative to output the laser pulses and the imaging pulses to a target area; and
   a controller in communication with the laser source and the imaging source, the controller operative to coordinate the laser signal and the imaging signal such that each of the laser pulses and each of the imaging series are in non-overlapping time windows.

2. The laser ablation and imaging system of claim 1, wherein each of the plurality of laser pulses comprises a laser pulse width and each of the plurality of imaging series has imaging pulses comprising an imaging series pulse width.

3. The laser ablation and imaging system of claim 2, wherein the controller controls the laser pulse width and the imaging series pulse width.

4. The laser ablation and imaging system of claim 3, wherein the controller controls the laser pulse width and the imaging series pulse width such that the laser pulse width and the imaging series pulse width are different.

5. The laser ablation and imaging system of claim 4, wherein the laser pulse width is less than the imaging series pulse width.

6. The laser ablation and imaging system of claim 5, wherein each imaging pulse comprises an imaging pulse width, wherein the controller further controls the imaging pulse width.

7. The laser ablation and imaging system of claim 6, wherein the controller controls the imaging series pulse width and the imaging pulse width such that the imaging series pulse width and the imaging pulse width are different.

8. The laser ablation and imaging system of claim 7, wherein the imaging series pulse width is greater than the imaging pulse width.

9. The laser ablation and imaging system of claim 6, wherein the controller controls the laser pulse width and the imaging pulse width such that the laser pulse width and the imaging pulse width are different.

10. The laser ablation and imaging system of claim 9, wherein the laser pulse width is greater than the imaging pulse width.

11. The laser ablation and imaging system of claim 1, wherein the at least one delivery device includes a fiber optic catheter.

12. The laser ablation and imaging system of claim 1, wherein the imaging signal includes at least one of an ultrasonic signal and a light reflectance signal.

13. The laser ablation and imaging system of claim 1, wherein the laser signal includes an ultraviolet signal.

14. The laser ablation and imaging system of claim 1, wherein the at least one delivery device includes a light guide for outputting the laser signal and an imaging device for outputting the imaging signal, and the light guide is positioned near the imaging device.

15. The laser ablation and imaging system of claim 1, wherein the laser frequency and the imaging series frequency are the same.

16. The laser ablation and imaging system of claim 15, wherein the imaging pulse frequency and the imaging series frequency are different.

17. The laser ablation and imaging system of claim 1, wherein the imaging pulse frequency and the imaging series frequency are different.

* * * * *